(12) United States Patent
Sperl

(10) Patent No.: US 8,523,836 B2
(45) Date of Patent: Sep. 3, 2013

(54) DISPOSABLE ABSORBENT ARTICLE WITH FINGER TAB

(75) Inventor: Michael Donald Sperl, Waupaca, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 21 days.

(21) Appl. No.: 12/910,332

(22) Filed: Oct. 22, 2010

(65) Prior Publication Data

US 2012/0101469 A1   Apr. 26, 2012

(51) Int. Cl.
*A61F 13/49*   (2006.01)
*A61F 13/56*   (2006.01)
*A61F 13/60*   (2006.01)
*A61F 13/62*   (2006.01)

(52) U.S. Cl.
USPC .......... 604/390; 604/385.01; 604/385.03; 604/386; 604/391

(58) Field of Classification Search
USPC ......... 604/385.01, 385.03–385.05, 385.11, 604/385.13, 386, 389–391
See application file for complete search history.

(56) References Cited

U.S. PATENT DOCUMENTS

| | | | |
|---|---|---|---|
| 5,163,932 A | | 11/1992 | Nomura et al. |
| 5,312,387 A | | 5/1994 | Rossini et al. |
| 5,383,871 A | * | 1/1995 | Carlin et al. ............ 604/385.29 |
| 5,407,513 A | | 4/1995 | Hayden et al. |
| 5,516,567 A | * | 5/1996 | Roessler et al. ............ 428/40.1 |
| 5,531,732 A | * | 7/1996 | Wood ............................ 604/391 |
| 5,603,708 A | | 2/1997 | Seth |
| 5,603,794 A | * | 2/1997 | Thomas ........................ 156/256 |
| 5,624,420 A | | 4/1997 | Bridges et al. |
| 5,624,429 A | | 4/1997 | Long et al. |
| 5,873,870 A | * | 2/1999 | Seitz et al. ............. 604/385.04 |
| 5,885,269 A | * | 3/1999 | Boyer et al. .................. 604/386 |

(Continued)

FOREIGN PATENT DOCUMENTS

| | | |
|---|---|---|
| EP | 0 233 704 B1 | 7/1992 |
| WO | WO 96/04873 A1 | 2/1996 |
| WO | WO 2009144601 A2 * | 12/2009 |
| WO | WO 2009144603 A2 * | 12/2009 |

OTHER PUBLICATIONS

U.S. Appl. No. 12/910,384, filed Oct. 22, 2010, by Schilpp et al. for "Disposable Absorbent Article with Finger Tab without Compromising Stretch.".

(Continued)

*Primary Examiner* — Jackie Ho
*Assistant Examiner* — Kathryn E Ditmer
(74) *Attorney, Agent, or Firm* — Randall W. Fieldhack; David J. Arteman; R. Joseph Foster, III

(57) ABSTRACT

An absorbent includes inner and outer surfaces, an absorbent body disposed therebetween, and front waist, back waist, and crotch regions. The article also includes pairs of front and back side panels, each side panel having an attachment edge and a free edge, the front and back side panels being releasably attachable to define a wear configuration of the absorbent article. The article also includes a finger tab having a distal end, a tab line where the finger tab intersects the free edge, and a proximal end attached to the free edge, wherein the distal end has a distal end longitudinal midpoint, wherein the tab line has a tab line longitudinal midpoint, and wherein the distal end longitudinal midpoint is longitudinally offset from the tab line longitudinal midpoint.

11 Claims, 7 Drawing Sheets

(56) References Cited

U.S. PATENT DOCUMENTS

| | | |
|---|---|---|
| 6,210,389 B1 | 4/2001 | Long et al. |
| 6,213,991 B1* | 4/2001 | Kling et al. ............... 604/385.01 |
| 6,302,871 B1* | 10/2001 | Nakao et al. ............. 604/385.13 |
| 6,409,858 B1 | 6/2002 | Popp et al. |
| 6,447,628 B1 | 9/2002 | Couillard et al. |
| 6,478,785 B1* | 11/2002 | Ashton et al. ............ 604/385.01 |
| 6,508,797 B1* | 1/2003 | Pozniak et al. .......... 604/385.11 |
| 6,649,010 B2 | 11/2003 | Parrish et al. |
| 6,743,321 B2 | 6/2004 | Guralski et al. |
| 6,820,671 B2 | 11/2004 | Calvert |
| 6,915,829 B2 | 7/2005 | Popp et al. |
| 7,150,730 B2 | 12/2006 | Hasler et al. |
| 7,198,622 B2 | 4/2007 | Dahlgren |
| 7,214,287 B2 | 5/2007 | Shiomi et al. |
| 7,219,403 B2 | 5/2007 | Miyamoto et al. |
| 7,344,526 B2 | 3/2008 | Yang et al. |
| 2002/0032427 A1 | 3/2002 | Schmitz et al. |
| 2002/0095132 A1* | 7/2002 | Ashton et al. ................ 604/392 |
| 2002/0099353 A1 | 7/2002 | Olson |
| 2002/0138064 A1 | 9/2002 | Datta et al. |
| 2003/0055389 A1 | 3/2003 | Sanders et al. |
| 2003/0060794 A1 | 3/2003 | Olson |
| 2003/0120240 A1* | 6/2003 | Buell et al. ................ 604/385.01 |
| 2003/0199841 A1* | 10/2003 | Ashton et al. ............ 604/385.01 |
| 2004/0016499 A1 | 1/2004 | Miyamoto et al. |
| 2005/0175269 A1 | 8/2005 | Ashton et al. |
| 2006/0266465 A1 | 11/2006 | Meyer |
| 2006/0266466 A1 | 11/2006 | Meyer |
| 2007/0073261 A1 | 3/2007 | Ashton et al. |
| 2007/0083177 A1* | 4/2007 | Takino et al. ............. 604/385.01 |
| 2007/0256777 A1 | 11/2007 | Andrews |
| 2008/0262461 A1 | 10/2008 | De Dier et al. |
| 2008/0276439 A1 | 11/2008 | Andrews et al. |
| 2009/0247975 A1 | 10/2009 | LaVon et al. |

OTHER PUBLICATIONS

U.S. Appl. No. 12/910,364, filed Oct. 22, 2010, by Sperl for "Disposable Absorbent Article with Opening Tab.".

* cited by examiner

DISPOSABLE ABSORBENT ARTICLE WITH FINGER TAB

BACKGROUND

The present disclosure relates generally to absorbent articles intended for personal wear, and more particularly to disposable absorbent articles.

Many absorbent articles intended for personal wear, e.g., such as diapers, training pants, feminine hygiene products, adult incontinence products, bandages, medical garments and the like are designed to be sufficiently absorbent to pull moisture from liquid body exudates including urine, menses, blood, etc. away from the wearer to reduce skin irritation caused by prolonged wetness exposure. Diapers, as an example, are typically placed and secured on a wearer using a set of primary fastening tabs, such as adhesive tabs or mechanical (e.g., hook or loop) fastening system tabs and left in place to absorb insults as well as to contain fecal waste. When the diaper is to be disposed of, the caregiver will sometimes fold the diaper into a more compact configuration and secure the diaper in this configuration using the primary fastening tabs.

Training pants, unlike diapers, typically come pre-assembled in a wear configuration to more closely resemble conventional underpants. In particular, front and back waist regions of such training pants are typically attached at a seam either permanently or refastenably (such as by a primary fastening system) to define a wear configuration of the pants having a waist opening and leg openings.

For such articles where the attachment is refastenable, such as diapers and training pants, a caregiver can find the attachment difficult to open because the attachment is designed to withstand stresses placed on the attachment by movement of the wearer without pop-opens (separation of the fasteners) occurring. The addition of a finger tab that extends transversely from a side panel can assist a caregiver in opening the attachment.

A pant design advantageous for manufacturing is one that increases the ease of opening a mechanical fastener side seam by enabling the user to manipulate the tab in a less resistant longitudinal peel motion.

SUMMARY

There is a need, therefore, for a finger tab system provided on an absorbent article such as training pants for improved resistance to pop-opens, and for securing the article in a compact disposal configuration while providing a sufficient visual awareness to the consumer of the presence of such a fastening system and sufficient operability and use of such a fastening system.

Disclosed herein is a pant design that increases the ease of opening a mechanical fastener side seam by enabling the user to manipulate the tab in a longitudinal peel motion that is less resistant than a typical transverse peel motion.

In one aspect, an absorbent article for personal wear about a wearer's waist has a transverse axis and includes a liquid permeable inner surface for facing the wearer, an outer surface for facing away from the wearer, an absorbent body disposed therebetween, and a front waist region, a back waist region, and a crotch region extending longitudinally between and interconnecting the front and back waist regions. The article also includes a pair of front side panels attached to the front waist region and a pair of back side panels attached to the back waist region, each side panel having an attachment edge and a free edge, the front and back side panels being releasably attachable to define a wear configuration of the absorbent article having a waist opening and a pair of leg openings spaced from the waist opening, wherein the front and back side panels each extend from the waist opening to one of the leg openings. The article also includes a finger tab having a distal end, a tab line where the finger tab intersects the free edge of one of the front and back side panels, and a proximal end attached to the free edge of one of the front and back side panels, wherein the distal end has a distal end longitudinal midpoint, wherein the tab line has a tab line longitudinal midpoint, and wherein the distal end longitudinal midpoint is longitudinally offset from the tab line longitudinal midpoint.

In another aspect, an absorbent article for personal wear about a wearer's waist has an article transverse axis and includes a liquid permeable inner surface for facing the wearer, an outer surface for facing away from the wearer, an absorbent body disposed therebetween, and a front waist region, a back waist region, and a crotch region extending longitudinally between and interconnecting the front and back waist regions. The article also includes a pair of front side panels attached to the front waist region and a pair of back side panels attached to the back waist region, the front and back side panels being releasably attachable to define a wear configuration of the absorbent article having a waist opening and a pair of leg openings spaced from the waist opening, wherein the front and back side panels each extend from the waist opening to one of the leg openings. The article also includes a finger tab having a distal end, a tab line where the finger tab intersects the free edge of one of the front and back side panels, and a proximal end attached to the free edge of one of the front and back side panels, wherein the distal end has a distal end longitudinal midpoint, wherein the tab line has a tab line longitudinal midpoint, wherein the finger tab has a tab central axis connecting the distal end longitudinal midpoint and the tab line longitudinal midpoint, and wherein the tab central axis forms an acute angle with a line parallel to the transverse axis.

In still another aspect, an absorbent article for personal wear about a wearer's waist has an article transverse axis and includes a liquid permeable inner surface for facing the wearer, an outer surface for facing away from the wearer, an absorbent body disposed therebetween, and a front waist region, a back waist region, and a crotch region extending longitudinally between and interconnecting the front and back waist regions. The article also includes a pair of front side panels attached to the front waist region and a pair of back side panels attached to the back waist region, the front and back side panels being releasably attachable to define a wear configuration of the absorbent article having a waist opening and a pair of leg openings spaced from the waist opening, wherein the front and back side panels each extend from the waist opening to one of the leg openings. The article also includes a finger tab having a distal end, a tab line where the finger tab intersects the free edge of one of the front and back side panels, and a proximal end attached to the free edge of one of the front and back side panels, wherein the distal end has a distal end longitudinal midpoint, wherein the tab line has a tab line longitudinal midpoint, wherein the finger tab has a tab central axis connecting the distal end longitudinal midpoint and the tab line longitudinal midpoint, and wherein the tab central axis forms an acute angle with a line parallel to the transverse axis, wherein the finger tab has a recurve shape configured to be cut from a web of tab material without producing waste tab material.

Other features of the disclosure will be in part apparent and in part pointed out hereinafter. Other objects and advantages of the present disclosure will become more apparent to those skilled in the art in view of the following description and the accompanying drawings.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

Figure 1:
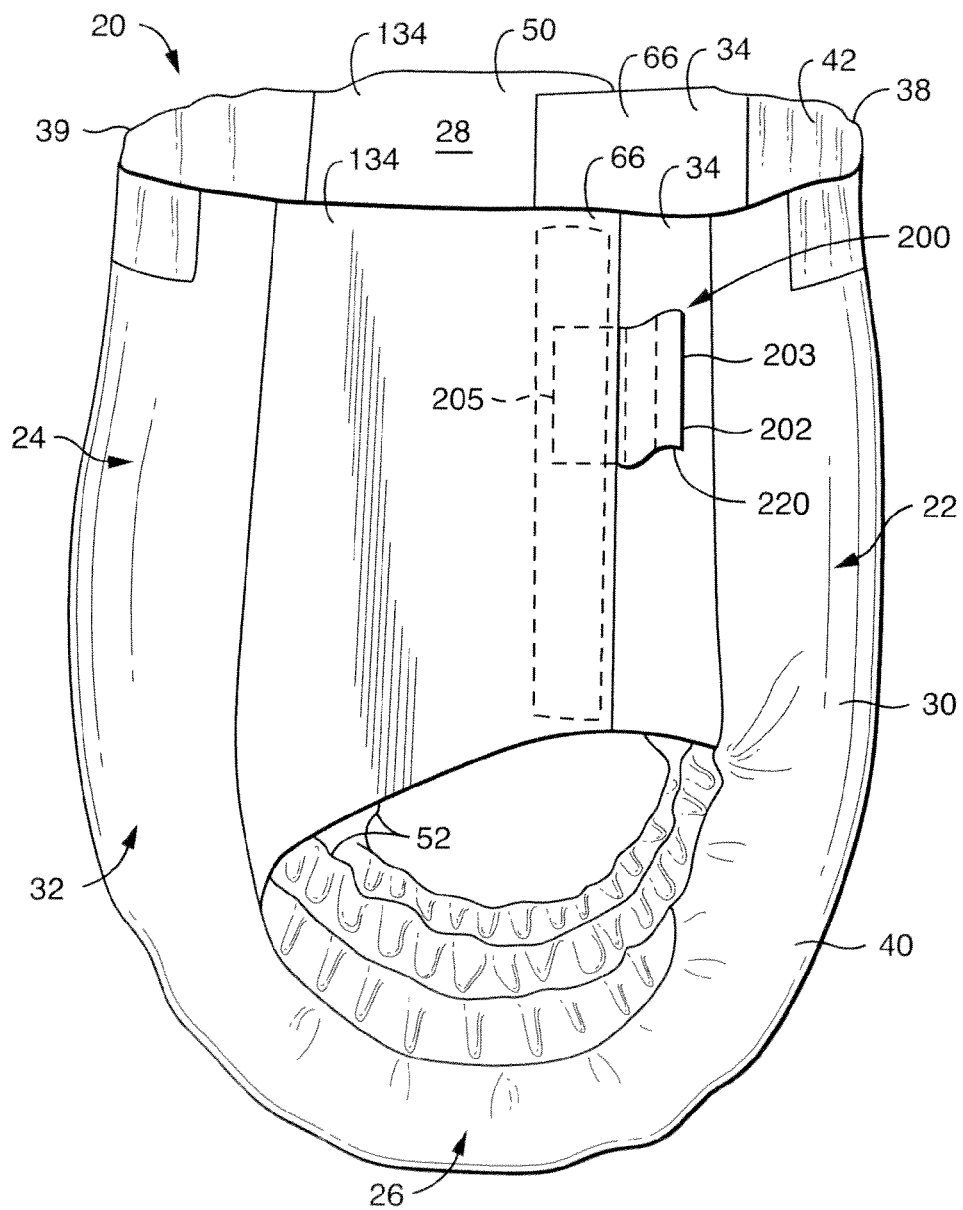
FIG. 1 is a side perspective of one aspect of a personal wear article in the form of a pair of training pants having a finger tab system illustrated in a fastened condition thereof.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

It is to be understood by one of ordinary skill in the art that the present discussion is a description of exemplary aspects of the present disclosure only, and is not intended as limiting the broader aspects of the present disclosure.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Cross direction" refers to the width of a fabric in a direction generally perpendicular to the direction in which it is produced, as opposed to "machine direction" that refers to the length of a fabric in the direction in which it is produced.

Figure 3:
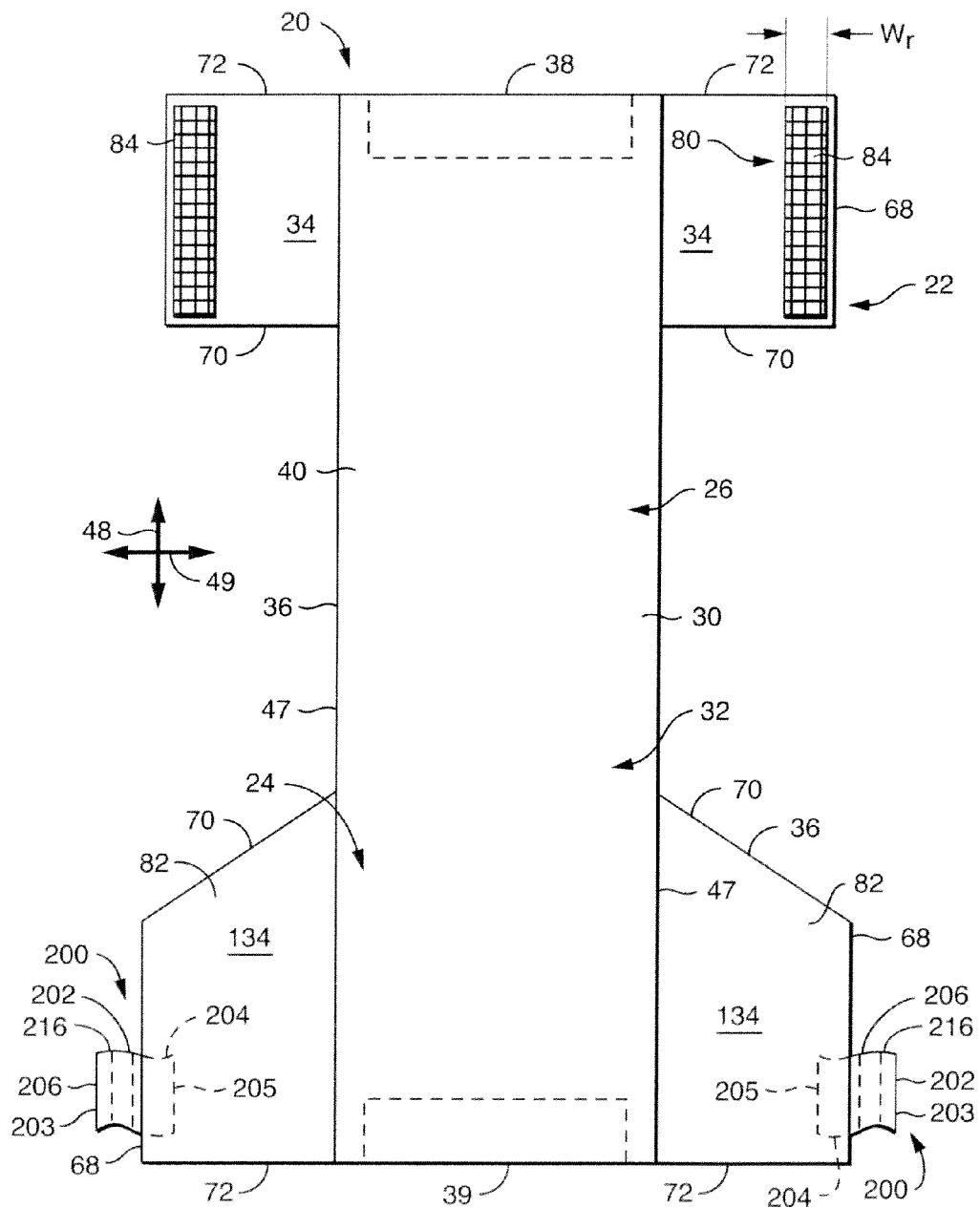
FIG. 3 is a bottom plan view of the training pants of FIG. 1 in an unfastened, unfolded and laid flat condition, and showing the surface of the training pants that faces away from the wearer.

"Cross direction assembly" refers to a process in which disposable absorbent products are manufactured in an orientation in which the products are connected side-to-side, in the transverse direction shown by arrow 49 in FIG. 3, a process utilizing a cross direction assembly entails products traveling through a converting machine parallel to the direction of arrow 49, as opposed to "machine direction assembly" in which the products are connected end-to-end or waist-to-waist.

"Disposable" refers to articles that are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite that can be elongated by at least 25 percent of its relaxed length and that will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Film" refers to a thermoplastic film made using a film extrusion and/or foaming process, such as a cast film or blown film extrusion process. The term includes apertured films, slit films, and other porous films that constitute liquid transfer films, as well as films that do not transfer liquid.

"Flexible" refers to materials that are compliant and that will readily conform to the general shape and contours of the wearer's body.

"Hydrophilic" describes fibers or the surfaces of fibers that are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "nonwettable" or hydrophobic.

"Integral" or "integrally" is used to refer to various portions of a single unitary element rather than separate structures bonded to or placed with or placed near one another.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, can spread or be transported parallel to the plane of the liquid impermeable layer or laminate, but this is not considered to be within the meaning of "liquid impermeable" when used herein.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

Figure 2:
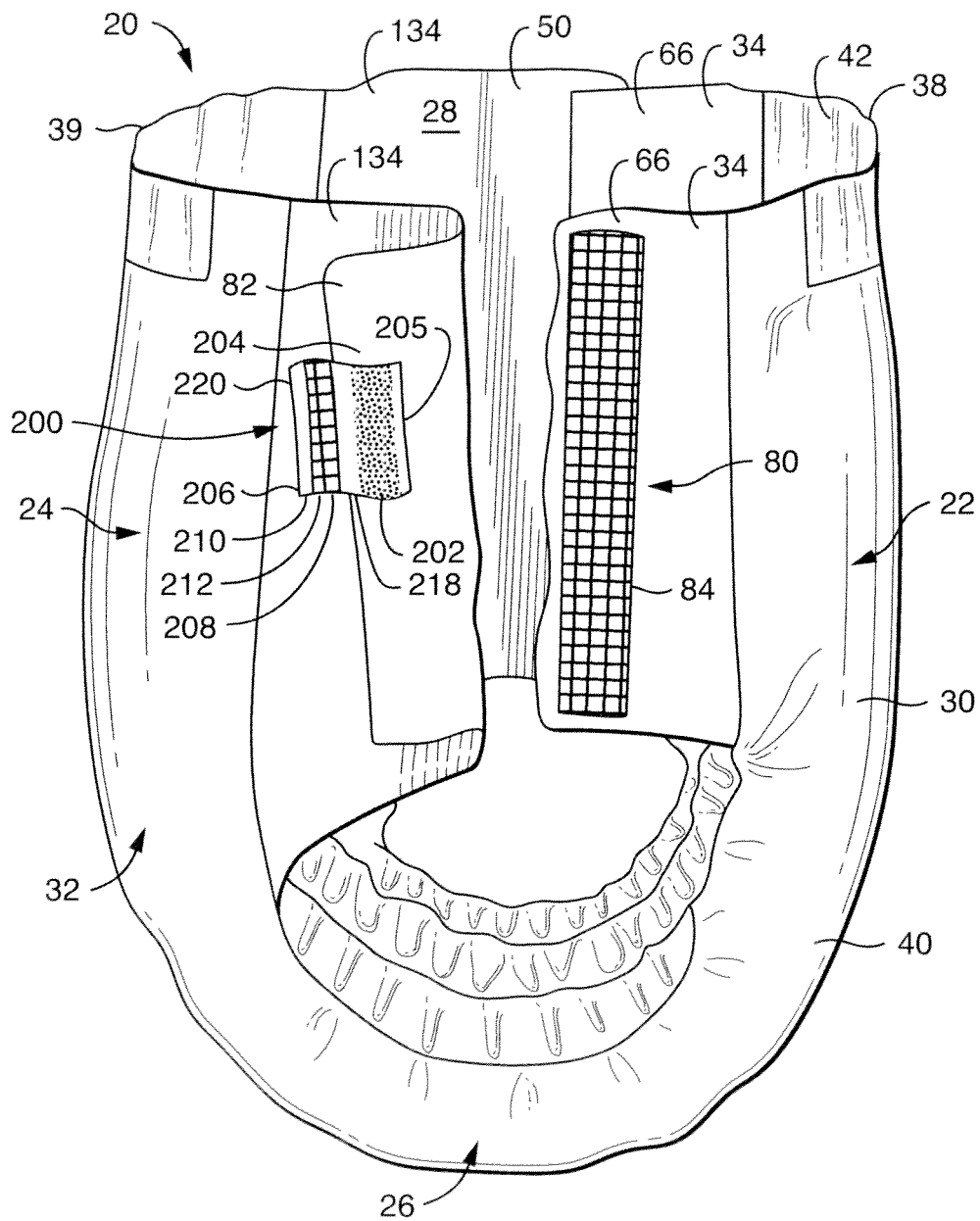
FIG. 2 is a side perspective similar to FIG. 1 with a primary, or article fastening system of the training pants in a unfastened condition on one side of the training pants and the finger tab system also in an unfastened condition.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Machine direction" refers to the length of a fabric in the direction in which it is produced, as opposed to "cross direction" that refers to the width of a fabric in a direction generally perpendicular to the machine direction.

"Machine direction assembly" refers to a process in which disposable absorbent products are manufactured in an orientation in which the products are connected end-to-end or waist-to-waist, in the longitudinal direction shown by arrow 48 in FIGS. 2 and 3, a process utilizing a machine direction assembly entails products traveling through a converting machine parallel to the direction of arrow 48, as opposed to "cross direction assembly" in which the products are connected side-to-side.

"Meltblown fiber" means fibers formed by extruding a molten thermoplastic material through a plurality of fine, usually circular, die capillaries as molten threads or filaments into converging high velocity heated gas (e.g., air) streams that attenuate the filaments of molten thermoplastic material to reduce their diameter, which can be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers that can be continuous or discontinuous, are generally smaller than about 0.6 denier, and are generally self bonding when deposited onto a collecting surface. Meltblown fibers used in the present disclosure are preferably substantially continuous in length.

"Member" when used in the singular can have the dual meaning of a single element or a plurality of elements.

"Nonwoven" and "nonwoven web" refer to materials and webs of material that are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Peel force" and "peel strain" refer to forces that tend to pull two adjoining bodies away from one another in opposite directions generally perpendicular to a plane in which the bodies are joined.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Shearing strain" refers to forces that tend to produce an opposite but parallel sliding motion between two bodies' planes.

"Spunbonded fiber" refers to small diameter fibers that are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 200% of its initial length, desirably to at least 250% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and that substantially returns to a nonsoftened condition when cooled to room temperature.

These terms can be defined with additional language in the remaining portions of the specification.

Referring now to the drawings and in particular to FIG. 1, a personal wear absorbent article according to one aspect is illustrated in the form of a pants-type article for wear about a wearer's waist, and more particularly in the form of children's toilet training pants, indicated in its entirety by the reference numeral 20. The term absorbent generally refers to articles that can be placed against or in proximity to the body of the wearer to absorb and/or retain various liquid wastes discharged from the body. The absorbent article can be disposable, which refers to articles that are intended to be discarded after a limited period of use instead of being laundered or otherwise restored for reuse. It is understood that the concepts described herein are suitable for use with various other pants-type articles such as adult incontinence articles, as well as other articles intended for personal wear such as clothing, diapers, feminine hygiene products, medical garments, surgical pads and bandages, other personal care or health care garments, and the like without departing from the scope of the present disclosure.

By way of illustration only, various materials and methods for constructing the training pants 20 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

Training pants typically do not have easy grasp point to open the side seam. A finger tab can be added to facilitate a grasping point. The present disclosure is directed to a process for making a pant-like absorbent garment having refastenable fasteners, such as hook and loop fasteners, on the side panels for ease of removal and donning of the absorbent garment without complete removal of a wearer's clothing. A pant design advantageous for either an end-to-end or side-by-side manufacturing process increases the ease of opening a mechanical fastener side seam by enabling the user to manipulate a finger tab in a less resistant longitudinal peel motion as compared to a more resistant transverse peel motion. Training pant mechanical fasteners typically have a longitudinal disengagement peel strength that is significantly less than the transverse disengagement peel strength. The transverse disengagement is done over a shorter distance, but its greater width requires a greater disengagement force per unit (e.g., mm) of peel. Conversely, the longitudinal disengagement is done over a greater distance, but its lesser width requires a lesser disengagement force per unit (e.g., mm) of peel.

Conventional refastenable tabs on refastenable side seam training pants lock up side panel stretch because the non-extensible hook on such tabs engages with an extensible side panel, thus reducing the amount of side panel material available for stretch. Less side panel material available for stretch then increases the force necessary to extend the material to a given extension point, increases the loading or stress at the side seam and causing a need to increase the side seam engagement strength to keep the side seam/pant closed. In addition, the greater side seam engagement strength requires the user to apply greater energy to disengage or open the side seam for removal of the training pants.

Conventional tabs on refastenable side seam training pants are also required to be robust in their materials and in their attachments because they act perpendicularly to the longitudinal axis of the side seam to open the article along a seam that is perpendicular and larger in width than the tab, thus requiring an attachment strength greater than the disengagement force needed to open the side seam. The side seam of refastenable side seam training pants is designed with an engagement strength sufficient to keep the side seam/pant closed during wear. When a caregiver grasps the tab in an attempt to open the side seam, the caregiver must apply enough force to overcome the engagement strength of the side seam. Such force is transmitted through the tab and its attachment; a greater engagement strength requires more disengagement force and, therefore, a tab more able to accommodate the increased force.

As a result of this relationship, tab robustness is related to the force necessary to open the seam. The engageable side seam shear strength likely represents the maximum force required to open the side seam during use. In a typical article, the peel disengagement is perpendicular to the longitudinal axis of the side seam, and the caregiver/tab is still acting against the greater longitudinal height of the fastener within the side seam.

What this means for training pant design is that refastenable side panel loading to extend is reduced by not locking up stretch. Reduced loading on the side seam means the side seam engagement strength can be lower without negatively impacting the frequency of side seam pop-opens. A lower required side seam engagement strength means that the side seam fasteners can use less fastening material such as less hook material, less aggressive hook material, lower bond strengths, fewer bond points, less adhesive, or some combination of these and other factors. A lower required side seam engagement strength also means that the force required to disengage the side seam is reduced.

As a result, the solution is to use a finger tab that operates in a motion that is not perpendicular to the longitudinal direction. A finger tab design with this motion allows for a less robust finger tab material and/or attachment strength and therefore a less robust finger tab. This solution reduces the amount of material and processing necessary for the finger tab.

The finger tab of the present application accomplishes this solution by providing a finger tab that acts other than perpendicularly to the longitudinal axis of the side seam.

The pair of training pants 20 is illustrated in FIG. 1 in a fully pre-assembled (i.e., as assembled during initial manufacture) configuration (broadly referred to herein as a wear configuration of the pants, i.e., absorbent article) and in FIG. 2 in a partially unfastened condition. The training pants 20 includes a front waist region 22, a back waist region 24, a crotch region 26 extending longitudinally between and interconnecting the front and back waist regions along a longitudinal direction of the pants, an inner surface 28 configured for contiguous relationship with the wearer, and an outer surface 30 opposite the inner surface. With additional reference to FIGS. 3 and 4, the training pants 20 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

Figure 4:
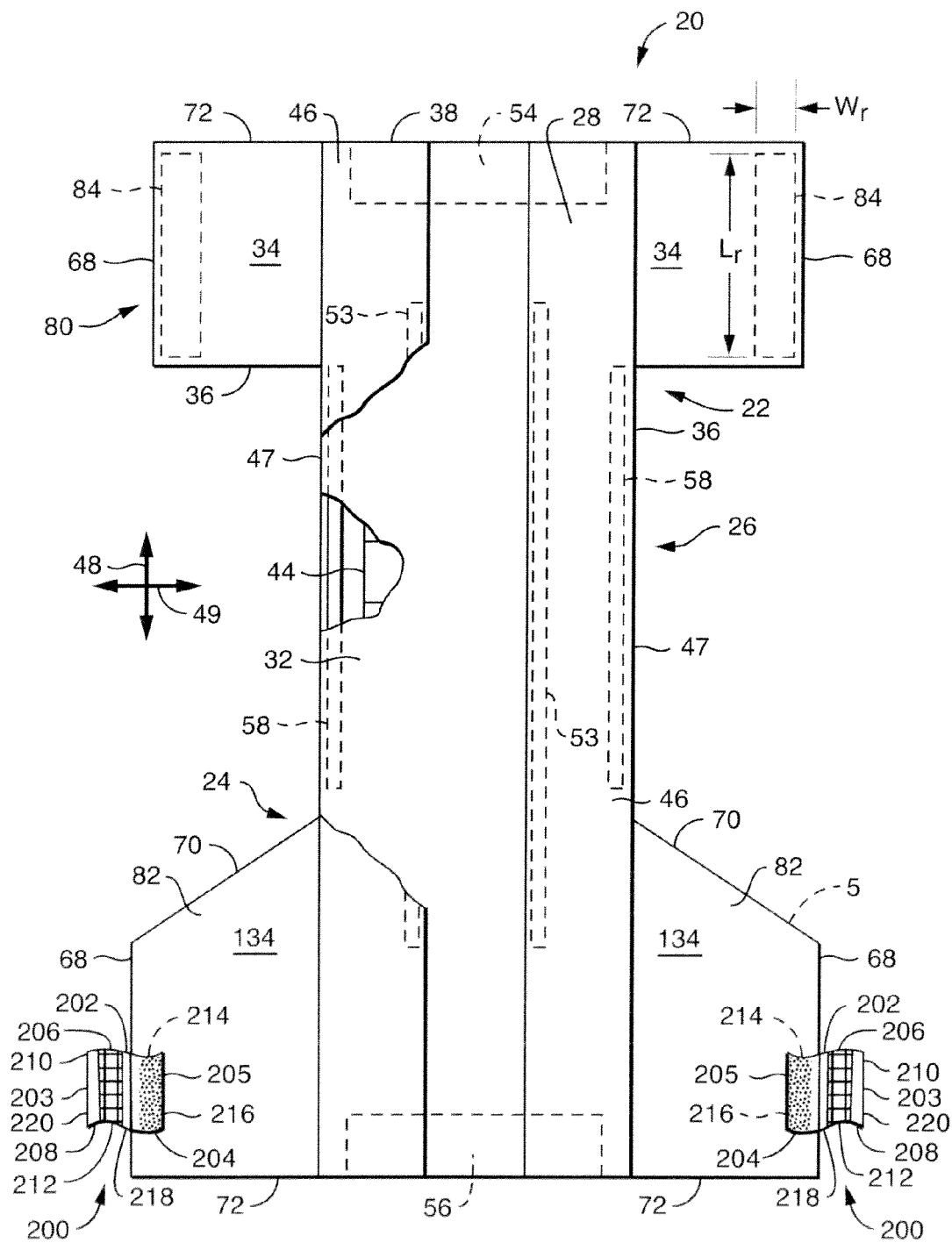
FIG. 4 is a top plan view similar to FIG. 3 showing the surface of the training pants that faces the wearer when worn and with portions cut away to show underlying features.

The illustrated pants 20 includes a central absorbent assembly, generally indicated at 32, which when laid flat as in FIGS. 3 and 4 can be rectangular or any other desired shape. A pair of laterally opposite front side panels 34 extends outward from the absorbent assembly 32 at the front waist region 22 (thereby forming transversely outer portions of the front waist region, and more broadly in part forming transversely opposite sides of the training pants). Laterally opposite back side panels 134 extend outward from the absorbent assembly 32 at the back waist region 24 (thereby forming transversely outer portions of the back waist region, and together with the front side panels 34 further defining the sides of the pants).

The central absorbent assembly 32 of the illustrated aspect includes an outer cover 40 and a bodyside liner 42 (FIGS. 1 and 2) connected to the outer cover in a superposed relation by suitable means such as adhesives, ultrasonic bonds, thermal bonds or other conventional techniques. An absorbent structure 44 (FIG. 4) is disposed between the outer cover and the bodyside liner. A pair of containment flaps 46 (FIG. 4) is secured to the bodyside liner 42 for inhibiting the lateral flow of body exudates. The central absorbent assembly 32 has opposite ends that form portions of the front and back waist edges 38 and 39, and opposite side edges 47 that form portions of the side edges 36 of the training pants 20 (FIGS. 3 and 4).

The absorbent assembly 32 and side panels 34, 134 can include two or more separate elements, as shown in FIGS. 1 and 2, or they can be integrally formed. Integrally formed side panels 34, 134 and absorbent assembly 32 would include at least some common materials, such as the bodyside liner, flap composite, outer cover, other materials and/or combinations thereof, and could define a one-piece elastic, stretchable, or nonstretchable pants 20. For further reference, arrows 48 and 49 in FIGS. 3 and 4 depict the orientation of a longitudinal axis and a transverse or lateral axis, respectively, of the training pants 20.

With the training pants 20 in the fastened condition as illustrated fully in FIG. 1 and partially in FIG. 2, the front and back side panels 34, 134 are attached to each other by a primary, or article fastening system 80 to define the pre-assembled three-dimensional wear configuration of the pants, having a waist opening 50 and a pair of leg openings 52. The front waist region 22 includes the portion of the training pants 20 that, when worn, is positioned at least in part on the front of the wearer while the back waist region 24 includes the portion of the training pants that is positioned at least in part on the back of the wearer. The crotch region 26 of the training pants 20 includes the portion of the training pants 20 that is positioned between the legs of the wearer and covers the lower torso of the wearer.

The front and back side panels 34 and 134 include the portions of the training pants 20 (and more particularly of the front and back waist regions 22, 24) that, when worn, are positioned on the hips of the wearer. The attached side panels 34, 134 thus broadly define the transversely opposite sides of the pants 20 at an engagement seam 66 along which the fastening system 80 releasably attaches the front and back side panels. The waist edges 38 and 39 of the training pants 20 are configured to encircle the waist of the wearer and together define the waist opening 50 (FIG. 1). Portions of the side edges 36 in the crotch region 26 generally define the leg openings 52.

The central absorbent assembly 32 is configured to contain and/or absorb exudates discharged from the wearer. For example, the containment flaps 46 are configured to provide a barrier to the transverse flow of body exudates. A flap elastic member 53 (FIG. 4) can be operatively joined with each containment flap 46 in any suitable manner as is well known in the art. The elasticized containment flaps 46 define a partially unattached edge that assumes an upright configuration in at least the crotch region 26 of the training pants 20 to form a seal against the wearer's body. The containment flaps 46 can be located along the side edges 36 of the pants 20, and can extend longitudinally along the entire length of the absorbent assembly 32 or can only extend partially along the length of the absorbent assembly. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 also suitably includes a front waist elastic member 54 (FIG. 4), a rear waist elastic member 56, and leg elastic members 58, as are known to those skilled in the art. The waist elastic members 54 and 56 can be attached to the outer cover 40 and/or the bodyside liner 42 along the opposite waist edges 38 and 39, and can extend over part or all of the waist edges. The leg elastic members 58 can be attached to the outer cover 40 and/or the bodyside liner 42 along the opposite side edges 36 and positioned in the crotch region 26 of the training pants 20. The leg elastic members 58 can be longitudinally aligned along each side edge 47 of the absorbent assembly 32.

The outer cover 40 suitably includes a material that is substantially liquid impermeable. The outer cover 40 can be a single layer of liquid impermeable material, but more suitably includes a multi-layered laminate structure in which at least one of the layers is liquid impermeable. The inner layer of the outer cover 40 can be both liquid and vapor impermeable, or it can be liquid impermeable and vapor permeable.

It is also contemplated that the outer cover 40 can be stretchable, and more suitably elastic. In particular, the outer cover 40 is suitably stretchable and more suitably elastic in at least the transverse or circumferential direction of the pants 20. In other aspects the outer cover can be stretchable, and more suitably elastic, in both the transverse and the longitudinal direction.

The liquid permeable bodyside liner 42 is illustrated as overlying the outer cover 40 and absorbent core 44, and can, but need not, have the same dimensions as the outer cover 40. The bodyside liner 42 is suitably compliant, soft feeling, and non-irritating to the child's skin. Further, the bodyside liner 42 can be less hydrophilic than the absorbent structure 44 to present a relatively dry surface to the wearer and permit liquid to readily penetrate through its thickness. Alternatively, the bodyside liner 42 can be more hydrophilic or can have essentially the same affinity for moisture as the absorbent structure 44 to present a relatively wet surface to the wearer to increase the sensation of being wet. This wet sensation can be useful as a training aid. The hydrophilic/hydrophobic properties can be varied across the length, width and/or depth of the bodyside liner 42 and absorbent structure 44 to achieve the desired wetness sensation or leakage performance.

The bodyside liner 42 can also be stretchable, and more suitably elastic. In particular, the bodyside liner 42 is suitably stretchable and more suitably elastic in at least the transverse 49, or circumferential direction of the pants 20. In other aspects, the bodyside liner 42 can be stretchable, and more suitably elastic, in both the transverse 49 and the longitudinal 48 directions.

As noted previously, the illustrated training pants 20 have front and back side panels 34 and 134 defining transversely opposite sides of the pants in the wear configuration of the pants. The side panels 34, 134 can be permanently attached along seams 66 to the central absorbent assembly 32 in the respective front and back waist regions 22 and 24. More particularly, as seen best in FIGS. 2 and 3, the front side panels 34 can be permanently attached to and extend transversely outward beyond the side edges 47 of the absorbent assembly 32 in the front waist region 22, and the back side panels 134 can be permanently attached to and extend transversely outward beyond the side edges of the absorbent assembly in the back waist region 24. The side panels 34 and 134 can be attached to the absorbent assembly 32 using attachment means known to those skilled in the art such as adhesive, thermal, pressure or ultrasonic bonding. Alternatively, the side panels 34 and 134 can be formed as an integral portion of a component of the absorbent assembly 32. For example, the side panels can include a generally wider portion of the outer cover 40, the bodyside liner 42, and/or another component of the absorbent assembly 32.

The front and back side panels 34, 134 each have an outer edge 68 spaced laterally from the seam 66, a leg end edge 70 disposed toward the longitudinal center of the training pants 20, and a waist end edge 72 disposed toward a longitudinal end of the training pants. The leg end edge 70 and waist end edge 72 extend from the side edges 47 of the absorbent assembly 32 to the outer edges 68. The leg end edges 70 of the side panels 34 and 134 form part of the side edges 36 of the training pants 20. The leg end edges 70 of the illustrated aspect are suitably curved and/or angled relative to the transverse axis 49 to provide a better fit around the wearer's legs. However, it is understood that only one of the leg end edges 70 can be curved or angled, such as the leg end edge of the back waist region 24, or neither of the leg end edges can be curved or angled, without departing from the scope of this disclosure. The waist end edges 72 are suitably parallel to the transverse axis 49. The waist end edges 72 of the front side panels 34 form part of the front waist edge 38 of the training pants 20, and the waist end edges 72 of the back side panels 134 form part of the back waist edge 39 of the pants.

The side panels 34, 134 suitably, although not necessarily, include a stretchable material capable of stretching in a direction generally parallel to the transverse axis 49 of the training pants 20. More suitably the side panels 34, 134 include an elastic material. Suitable elastic materials, as well as one process of incorporating stretchable side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; 5,104,116 issued Apr. 14, 1992 to Pohjola; and U.S. Pat. No. 5,046,272 issued Sep. 10, 1991 to Vogt et al.; all of which are incorporated herein by reference. In particular aspects, the stretch material can include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference. Other suitable materials are described in U.S. patent application Ser. Nos. 12/649,508 to Welch et al. and 12/023,447 to Lake et al., all of which are incorporated herein by reference.

Alternatively, the side panel material can include other woven or nonwoven materials, such as those described above as being suitable for the outer cover 40 or bodyside liner 42; mechanically pre-strained composites; or stretchable but inelastic materials.

The absorbent structure 44 can be any structure that is generally compressible, conformable, non-irritating to the wearer's skin and capable of absorbing and retaining liquid body exudates, and can be manufactured in a wide variety of sizes and shapes, and from a wide variety of absorbent materials commonly used in the art.

The article fastening system 80 includes laterally opposite first article fastening components 82 adapted for refastenable engagement to corresponding second article fastening components 84. In one aspect, a front or outer surface of each of the article fastening components 82, 84 includes a plurality of engaging elements. The engaging elements of the first article fastening components 82 are adapted to repeatedly engage and disengage corresponding engaging elements of the second article fastening components 84 to releasably secure the pants 20 in its three-dimensional configuration. The article fastening system 80 provides an attachment of a strength sufficient to maintain the article in a wear configuration during use of the pants 20 by the wearer.

The article fastening components 82, 84 can include any refastenable fasteners suitable for absorbent articles, such as adhesive fasteners, cohesive fasteners, mechanical fasteners, or the like. In particular aspects, the article fastening components 82, 84 include mechanical fastening components for improved performance. Suitable mechanical fastening components can be provided by interlocking geometric shaped materials, such as hooks, loops, bulbs, mushrooms, arrowheads, balls on stems, male and female mating components, buckles, snaps, or the like.

In the illustrated aspect, the first article fastening components 82 (i.e., one on each side of the training pants 20) include loop fasteners and the second article fastening components 84 include complementary hook fasteners. Alternatively, the first article fastening components 82 can include hook fasteners and the second article fastening components 84 can include complementary loop fasteners. In another aspect, the article fastening components 82, 84 can include interlocking similar surface fasteners, or adhesive and cohesive fastening elements such as an adhesive fastener and an adhesive-receptive landing zone or material; or the like. Although the training pants 20 illustrated in FIG. 1 show the back side panels 134 overlapping the front side panels 34 upon connection thereto, which is convenient, the training pants 20 can also be configured so that the front side panels overlap the back side panels when connected. One skilled in the art will recognize that the shape, density and polymer composition of the hooks and loops can be selected to obtain the desired level of engagement between the article fastening components 82, 84. A more aggressive hook material can include a material with a greater average hook height and/or a greater percentage of directionally-aligned hooks. When engaged, the article fastening components 82, 84 of the illustrated aspect define the refastenable engagement seams 66 (FIG. 2).

As discussed above, in one particularly suitable aspect, as best seen in FIGS. 2 and 4, the back side panels 134 are constructed so that the inner surfaces of the respective back side panels define loop article fastening components 82 (i.e., the back side panels 134 and the article fastening components 82 are formed integrally). It is understood, however, that the loop article fastening components 82 can be formed separate from the back side panels 134 and attached thereto, such as by adhesive, thermal bonds, ultrasonic bonds, pressure bonds or other suitable techniques without departing from the scope of this disclosure.

An easy opening side (EOS) finger tab is attached to and overhangs the cross-direction side panel edge for ease of opening. This easy opening side design causes the user to grab and pull the EOS tab in a machine-direction, longitudinal peel motion. A typical side seam attachment/engagement zone has a longitudinal length four times greater than its transverse width. As a result, a longitudinal motion peel motion requires at least four times less energy to open the side seam as compared to a transverse or cross-direction peel motion. A cut-in-place type of operation well known in the business can place the EOS tab at the panel edge such that the EOS tab feature extends from the pant edge. This enables the user to grab and pull in a longitudinal motion.

Figure 5:
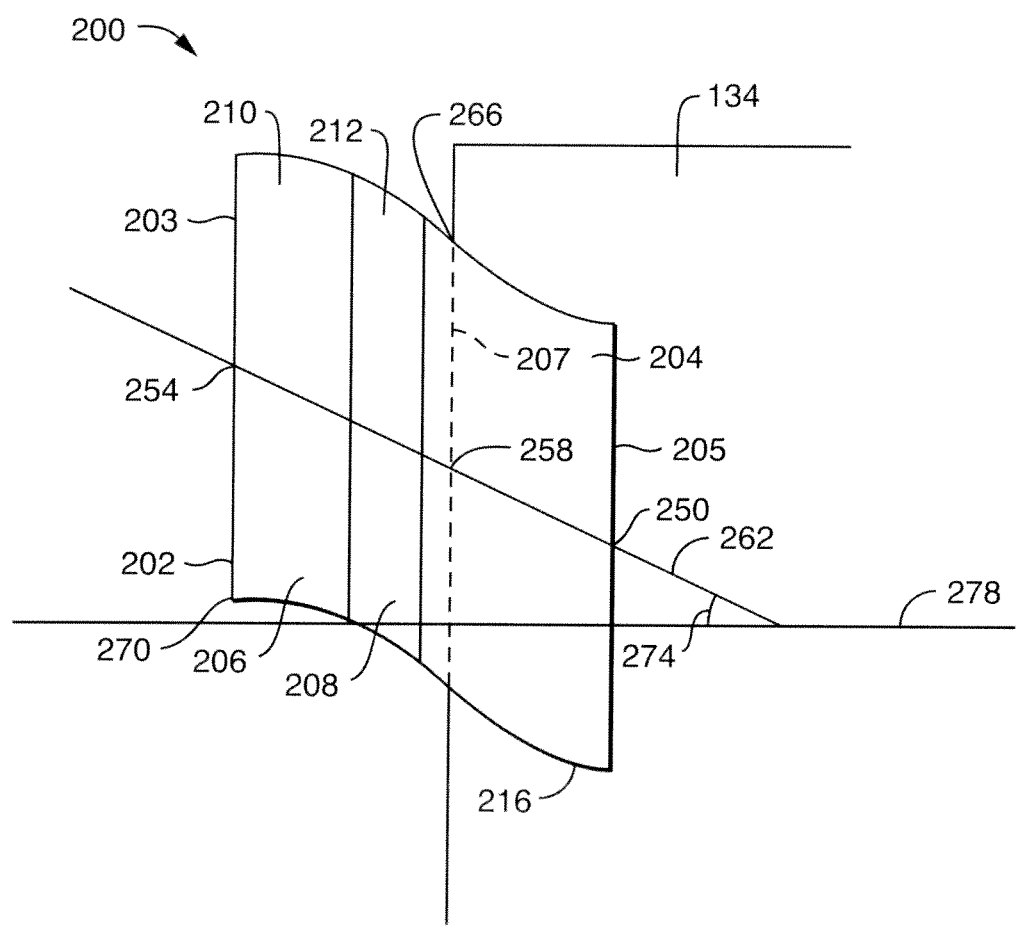
FIG. 5 is a partial schematic view of the finger tab system illustrated in FIGS. 1-4.

With particular reference now to FIGS. 1, 2, and 5, a secondary, or finger tab system, generally indicated at 200, is provided for use in opening the side seam 66 of the training pants 20. As illustrated in FIGS. 2 and 4, the finger tab system includes a tab 202 attached to each of the back side panels 134 (broadly, to the transversely opposite sides of the training pants 20) and extending in part transversely outward of the respective back side panels for opposed relationship with the corresponding front side panels in the wear configuration of the pants. As seen best in FIGS. 5-7, each finger tab 202 has a distal end 203, a distal corner 220 (see FIGS. 1, 2, and 4), and a proximal end 205, and includes an attachment region 204 generally at the proximal end 205 and at which the finger tab 202 is attached 214 (see FIG. 4) to the respective back side panel 134, and a tab region 206 generally at the distal end 203 and extending transversely outward from the attachment region 204. The finger tab 202 forms a tab line 207 where the finger tab 202 intersects the front or back side panel 34, 134. More suitably, the tab region 206 of the finger tab 202 can include at least one tab fastener region 208 having a tab fastening component 212 for use in securing the finger tab 202 to the training pants 20, and can further include a grip region 210 transversely outward of the tab fastener region 208 for use in manually gripping and manipulating the finger tab 202 relative to the pants 20.

The tab region 206 via its fastener region 208 can be releasably attached to a side panel when the pants 20 is in a wear configuration. Such a releasable attachment by the tab region 206 alone, however, provides an attachment strength that is insufficient to maintain the pants 20 in a wear configuration during use of the pants 20 by the wearer.

The attachment region 204 has an attachment height, which is the longitudinal height of the finger tab 202 in the attachment region 204. The longitudinal height of the finger tab 202 in the attachment region 204 also includes a proximal end longitudinal midpoint 250. The tab region 206 has a tab region longitudinal height, which is the longitudinal height of the finger tab 202 in the tab region 206. The longitudinal height of the finger tab 202 in the tab region 206 also includes a distal end longitudinal midpoint 254. The tab line 207 has a tab line longitudinal height, which is the longitudinal height of the finger tab 202 along the tab line 207. The tab line height also includes a tab line longitudinal midpoint 258. A tab central axis 262 connects the tab line longitudinal midpoint to the distal end longitudinal midpoint.

In one aspect of the present disclosure, the distal end longitudinal midpoint 254 is longitudinally offset from the tab line longitudinal midpoint 258. This arrangement enables the pulling force applied from the finger tab 202 to the seam 66 to be applied at an angle other than perpendicular to the seam 66. In another aspect, the distal end longitudinal midpoint 254 is further longitudinally offset from the article transverse axis 49 than is the tab line longitudinal midpoint 258. In still another aspect, the tab line longitudinal midpoint 258 is further longitudinally offset from the article transverse axis 49 than is the distal end longitudinal midpoint 254. In yet another aspect, the tab line has a tab line upper end 266, the finger tab distal end has a distal end lower edge 270, and the distal end lower edge 270 is further longitudinally offset from the article transverse axis 49 than is the tab line upper end 266. Conversely, the tab line upper end 266 can be further longitudinally offset from the article transverse axis 49 than is the distal end lower edge 270.

In alternate aspects of the present disclosure, the finger tab 202 can extend longitudinally beyond the waist edge 38, 39 of the pants 20, or the finger tab 202 can be disposed such that it does not extend longitudinally beyond the waist edge 38, 39 of the pants 20. Finally, the longitudinal height of the distal end 203 of the finger tab 202 can be equal to the longitudinal height of the tab line 207. In other aspects, the longitudinal height of the distal end 203 of the finger tab 202 can be greater than the longitudinal height of the tab line 207, or the longitudinal height of the distal end 203 of the finger tab 202 can be less than the longitudinal height of the tab line 207.

In another aspect of the present disclosure, the tab central axis 262 connecting the distal end longitudinal midpoint 254 and the tab line longitudinal midpoint 258 forms an acute angle 274 with a line 278 parallel to the transverse axis 49. This arrangement enables the pulling force applied from the finger tab 202 to the seam 66 to be applied at an angle other than perpendicular to the seam 66. In various aspects, the acute angle 274 is greater than 10 degrees, greater than 20 degrees, greater than 30 degrees, greater than 45 degrees, or greater than 60 degrees.

Figure 6:
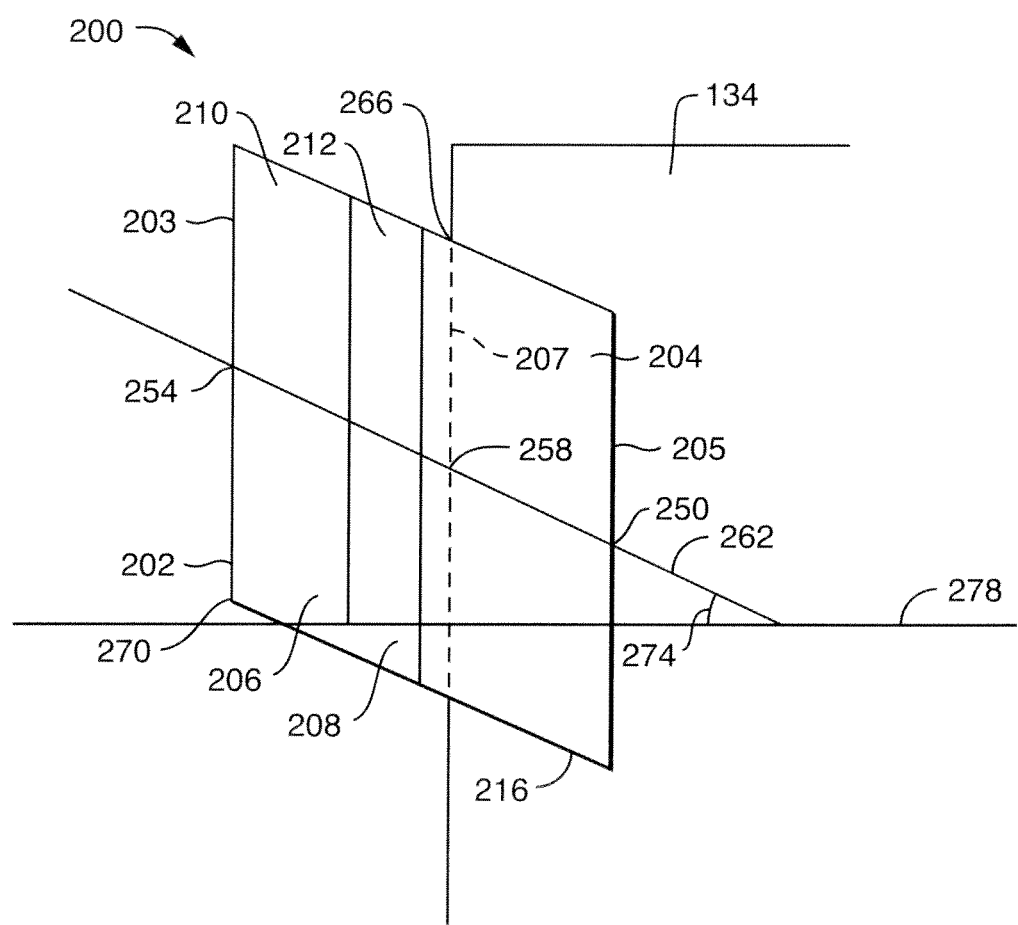
FIG. 6 is a partial schematic view of an alternative to the finger tab system illustrated in FIGS. 1-4.
Figure 7:
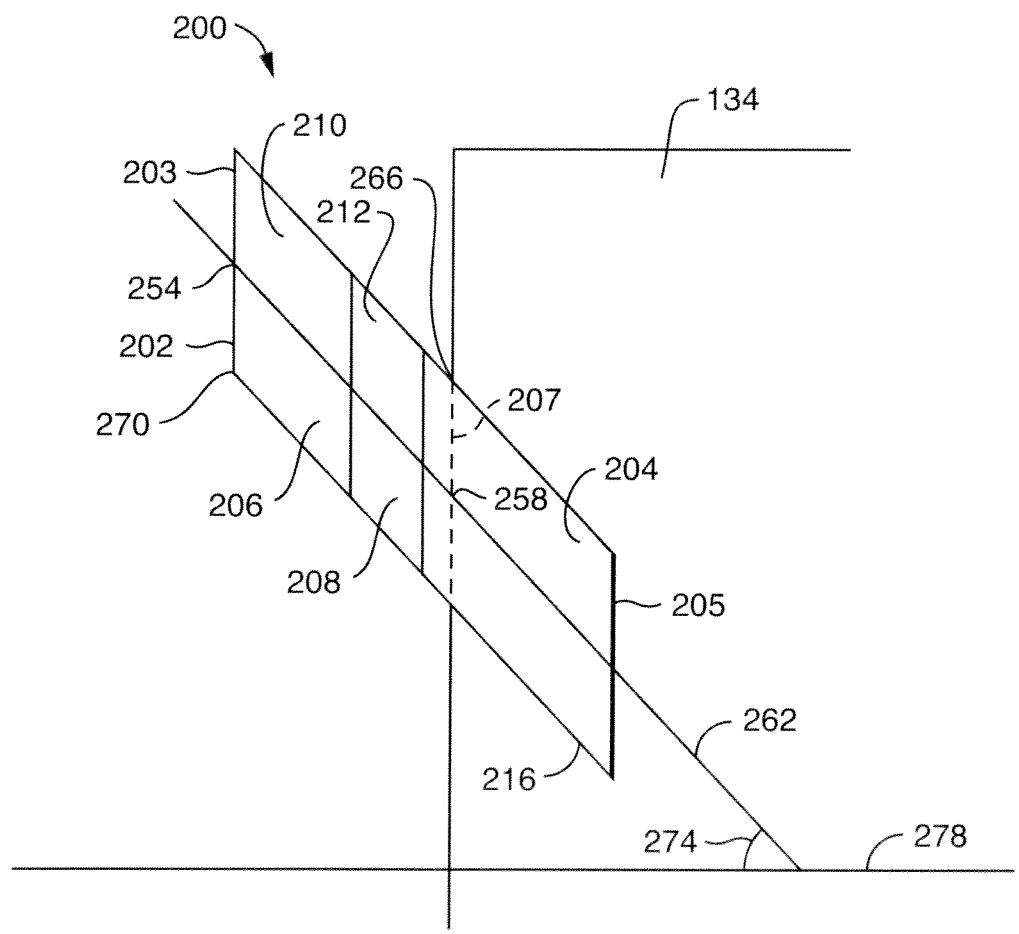
FIG. 7 is a partial schematic view of an alternative to the finger tab system illustrated in FIGS. 1-4.

In one aspect of the present disclosure, as illustrated in FIG. 5, the finger tab 202 is substantially a recurve shape that allows the finger tab 202 to be cut from a web, a sheet, or a roll with little to no loss of material, particularly in view of the material waste inherent in a conventional arcuate or sinusoidal tab shape. Also, the recurve shape of the finger tab 202 allows a wearer or caregiver to easily access and lift the tab region 206 of the finger tab 202 that is otherwise releasably attached to the pants 20. Finally, the recurve shape of the finger tab 202 reduces the likelihood of the finger tab 202 being torn from the pants 20 during use or readjustment of the pants 20. In other aspects of the present disclosure, as illustrated in FIGS. 6 and 7, the shape of finger tab 202 is generally rhomboid. In alternative aspects of the present disclosure, the finger tab 202 can have any shape that meets the requirements described herein.

The tab fastening component 212, if present, of the illustrated tab fastener region 208 includes a hook fastener. The tab fastener region 208 can include one, two, or more lanes or rows of hook material. The outer surface of each front side panel 34 suitably defines a corresponding fastening component, e.g., a loop fastener, to permit the finger tab 202 on each side of the pants 20 to be attached at its tab fastener region 208 to the respective front side panel (i.e., broadly, to the pants 20) in the wear configuration of the pants 20. For example, the front side panel 34 in one particularly suitable aspect can be constructed of vertical filament laminate material (VFL) as described previously so that the outer surface of the front side panel 34 itself defines a loop fastening component. Alternatively, a loop fastener component (not shown) can be formed separately from the front side panel 34 and attached to the panel outer surface without departing from the scope of this disclosure. The outer facing surface 30 of the outer cover 40 of the pants 20 is also suitably constructed to define a loop fastener, such as by forming the outer cover of a material that defines a loop fastening component (e.g., VFL or other suitable material) or by forming a separate loop fastening component and attaching it to the outer surface of the pants outer cover, to permit attachment of the finger tab 202 to the outer cover in the disposal configuration of the pants 20.

It is understood that the tab fastening component(s) 212 defining the one or more tab fastener regions 208 of the finger tab 202 can instead be a loop fastener component, with the outer surfaces of the front side panels 34 and outer cover 40 of the pants 20 being constructed to define corresponding hook fastening components. In other aspects, the tab fastening component 212 defining the tab fastener region(s) 208 and the outer surfaces of the front side panels 34 and pants outer cover 40 can include other suitable releasably attachable fasteners without departing from the scope of this disclosure. It is also contemplated that the tab fastening component 212 defining the tab fastener region 208 can be releasably attachable to the pants 20 (e.g., to the front side panel 34) in the wear configuration but otherwise more permanently attachable elsewhere on the pants (e.g., to the outer cover 40) in the disposal configuration of the pants. The term permanent attachment is intended herein to refer to an attachment that is generally not releasable without some damage or substantially reduced ability to reattach to the fastening component and/or the component to which the fastening component is attached.

In one alternative aspect, the tab region 206 of the finger tab 202 includes at least one gap region 218 between the attachment region 204 and the tab fastener region 208 to allow for manufacturing tolerances in preventing the tab fastening component 212 from being attached to the side panel. In other words, the gap region 218 allows the tab fastener region 208 to be free from bonding to the pants 20. Such an arrangement further reduces the opportunity for hook-on-hook interface between the tab fastening component 212 and the article fastening system 80.

In the illustrated aspect, the finger tabs 202 attach to the outer surfaces of the front side panels 34 (e.g., outer surface 30 of pants 20) in the wear configuration of the article. It is contemplated that in the wear configuration the finger tabs 202 can be configured to attach to the inner surfaces of the front side panels 34 (e.g., inner surface 28 of pants 20) and remain within the scope of this disclosure.

The attachment region 204 of each finger tab 202 is suitably attached to the respective back side panel 134 (broadly, to the respective side of the pants 20) and in the illustrated aspect is attached to the inner surface of the back side panel. It is understood, however, that the attachment region 204 can instead be attached to the outer surface of the back side panel 134. The attachment region 204, in the aspect in which the back side panel 134 overlaps the front side panel 34, is more suitably attached to the back side panel adjacent the transverse edge of the back side panel. But the attachment region 204 can instead be attached to the back side panel 134 more transversely distal from the transverse edge of the back side panel, such as when the front side panel 34 overlaps the back side panel, without departing from the scope of this disclosure.

The attachment region 204 of each finger tab 202 is suitably attached to the inner surface of the back side panel 134, such as by adhesive, thermal bonding, ultrasonic bonding, pressure bonding, or other suitable attachment technique. More suitably, an attachment face 214 (FIG. 4) of each finger tab 202 is attached to the inner surface of the back side panel 134 at the attachment region 204 of the tab. The tab region 206 of each finger tab 202 extends transversely outward of the attachment region 204 into overlapping or opposed relationship with the outer surface of the corresponding front side panel 34 so that the tab region is accessible exterior of the pants 20 in the wear configuration of the pants. It is understood, however, that the tab region 206 can instead be in opposed relationship with and releasably attachable to the inner surface of the front side panel 34 without departing from the scope of this disclosure.

In another aspect, the tab region 206 of each finger tab 202 is suitably positioned generally longitudinally offset along the length of the side of the pants 20 (e.g., between the waist opening 50 and respective leg opening 52), and in particular at the engagement seam 66 between the front and back side panels 34, 134. For processing ease and aiding performance attributes associated with the finger tab 202, the finger tab 202 is positioned at least 5 mm from the waist opening 50 of the pants 20.

The tab fastener region 208 of each finger tab 202 suitably extends lengthwise of the tab, within the tab region 206 thereof, to the edges of the finger tab 202 at the tab region 206. It is understood, however, that the fastener region 208 need not extend the full length of the finger tab 202 at the tab region 206 to remain within the scope of this disclosure.

When the finger tab 202 includes a grip region 210 such as in the illustrated aspect of FIGS. 1-7, the finger tab 202 is suitably constructed so that the grip region 210 is non-attachable to the pants 20, at least in the wear configuration of the pants 20. The term non-attachable as used in this instance means that the grip region 210 is not releasably or otherwise removably attachable to the pants 20 in the wear configuration thereof, nor is the grip region 210 permanently attached to the pants 20. In one aspect, the grip region 210 extends transversely outward from the tab fastener region 208 of each finger tab 202 a distance of at least about 1 mm, such as in the range of about 1 mm to about 10 mm to provide sufficient unattached material of the tab for readily gripping and pulling on the tab.

In one aspect, each finger tab 202 is suitably constructed of a base substrate 216 having a tab fastening component 212 (e.g., a hook fastening component in the illustrated aspect) attached thereto such as by adhesive bonding, thermal bonding, ultrasonic bonding, pressure bonding, or other suitable technique to define the tab fastener region 208 of the finger tab 202. In certain aspects, the base substrate 216 can be constructed such that, other than the fastener region 208, the finger tab 202 is not releasably attachable to the pants 20, particularly at the grip region 210 (if provided) of the finger tab 202. In one particularly suitable aspect, the base substrate 216 is less stretchable (at least in the transverse direction thereof) than the pants 20 (in the transverse, or circumferential direction thereof) and more suitably the base substrate is non-stretchable so that pulling on the tab transversely of pants 20 to secure the pants 20 in their disposal configuration the pants 20 (and in particular the back side panels 134) are allowed to stretch. As an example, one suitable material from which the base substrate 216 can be constructed is a three-layer nonwoven polypropylene material known as SMS. SMS is an acronym for Spunbond-Meltblown-Spunbond, the process by which the three layers are constructed and then laminated together. One example of an SMS material is described in U.S. Pat. No. 4,041,203 to Brock et al. It should be noted, however, that other nonwovens as well as other materials including wovens, films, foam/film laminates and combinations thereof can be used to construct the finger tab 202 without departing from the scope of this disclosure.

In particular aspects, the base substrate 216 is constructed of a material that is releasably attachable with the article fastener component 84 of the article fastening system 80. For example, in particular aspects, the base substrate 216 is formed from a material such as acrylic, polyamide, polyethylene, polypropylene or polyester, and is formed into a "loop"-type material by methods such as warp knitting, stitch bonding or needle punching. The base substrate 216 can include any fibrous structure capable of entangling or catching hook materials, such as carded, spunbonded or other nonwoven webs or composites, including elastomeric and nonelastomeric composites. One material suitable for use as a base substrate 216 is available from Guilford Mills, Inc., Greensboro, N.C., U.S.A. under the trade designation No. 36549. Another suitable base substrate material includes a pattern un-bonded web as disclosed in co-assigned U.S. Pat. No. 5,858,515 issued Jan. 12, 1999 to Stokes, et al., which is incorporated herein by reference to the extent consistent herewith. In particular aspects, the base substrate 216 can include a "loop"-type material as just discussed but that is attached to a backing structure, and the composite is then attached to the pants 20, such as along the side edges of the front or back side panels 34, 134.

As previously discussed, in particular aspects each of the transversely opposite sides of the pants 20 include a material (such as, for example, a nonwoven material) that is releasably engageable with the hook material of the primary fastening system. When the article is fastened in the wear configuration, it is possible in certain aspects that the hook material of article fastening system 80 simultaneously engages both the base substrate 216 and an outer facing of the transversely opposite sides of the article (such as, for example, the outermost nonwoven facing of an elastomeric nonwoven laminate). For example, if the greatest length of the attachment region 204 of the finger tab 202 is less than the greatest length of the engagement seam, it is probable that the refastenable seam 66 will be formed not only by engagement of the hook component to the base substrate 216, but also by engagement of the hook component to portions of the outer facing of the side panel 134 that extend beyond the longitudinal ends of the attachment region 204 of the finger tab 202.

Similarly, if the greatest width of the attachment region 204 of the finger tab 202 is less than the greatest width of the engagement seam, it is probable that the refastenable seam 66 will be formed not only by engagement of the hook component to the base substrate 216, but also by engagement of the hook component to portions of the outer facing of the side panel 134 that extend transversely inward of the longitudinal side edge of the attachment region 204 of the finger tab 202, as representatively illustrated in FIG. 1. However, it is not necessary that the hook material of the article fastening system 80 simultaneously engage both the disposal-tab base substrate 216 and the transversely opposite sides of the article. For example, if the greatest length of the attachment region 204 of the finger tab 202 is greater than the greatest length of the engagement seam, and/or if the greatest width of the attachment region 204 of the finger tab 202 is greater than that the greatest width of the engagement seam, the refastenable seam 66 can be formed solely by engagement of the hook component to the base substrate 216.

In use, the training pants 20 are constructed and pre-assembled in their wear configuration, with the article fastening system 80 releasably attaching the front and back waist regions 22, 24 (and more particularly the front and back side panels 34, 134 in the illustrated aspect). The tab fastener region 208 of each finger tab 202 is releasably attached to the outer surface of the respective front side panel 34 to releasably attach the tab region 206 of each finger tab 202 to the pants 20 in the wear configuration of the pants 20.

When the pants 20 are to be discarded after use, the pants 20 can be slipped off of the wearer in the manner of conventional underpants, or the front and back waist regions 22, 24 can be detached from each other (e.g., by separation of the article fastening components 82, 84 of the article fastening system 80) and the pants 20 removed from the wearer. Where the front and back waist regions 22, 24 are separated to remove the pants 20, the tab fastener regions 208 of the finger tabs 202 must be detached from the front waist region (e.g., from the front side panels 34). To detach the tab fastener regions 208 of the finger tabs 202 illustrated in the aspect of FIGS. 1-4, the grip region 210 of each finger tab 202 is gripped between the thumb and forefinger and pulled away from the front side panel 34 until the tab fastener region 208 breaks free from its attachment to the front side panel 34.

Peel Strength Test

The level of securement of any particular area of the finger tab or refastenable seam can be quantified using the following Peel Test method, which is designed to quantify, in grams, the peak and the average dynamic peel strength of the refastenable seam holding the front waist region of the absorbent article to the rear waist region, or of the connection between the finger tab and a side panel. The refastenable seam is used in this description as an example. The direction of removal or peel in this disclosure is that direction in which the fastener material would generally be removed from a substrate when the product is in use. This direction is in the transverse direction for a typical finger tab and more parallel to a longitudinal centerline of the product for the finger tab described herein.

Sample Preparation

The size of suitable samples of refastenable seam material having a single enhanced refastenable attachment zone can measure 7.6 cm. by 1.9 cm. (3 by 0.75 inch), with the enhanced refastenable attachment zone located 0.6 cm. (0.25 inch) inboard of one end edge. The size of the sample may need to be adjusted for different refastenable seam configurations.

Equipment

1. Constant rate of extension tensile tester equipped with an appropriate load cell. A suitable tensile testing system is a Sintech Tensile Tester, commercially available from MTS, Research Triangle Park, N.C., under the trade designation Sintech Model 1/G Tensile Tester.

2. Software commercially obtained from MTS under the trade designation MTS TESTWORKS® for Windows Version 3.10.

3. Pneumatic-action grips commercially available from Instron Corporation, Canton, Mass., under the trade designation Instron Model 2712-004.

4. 2.5 cm. by 10.1 cm. (1 by 4 inch) grip faces, rubber coated, commercially available from Instron Corporation, Canton, Mass.

5. Test facility having a temperature of 23±1° C., and a relative humidity of 50±2 percent.

Test Procedure

1. A sample to be tested is conditioned in the test facility for at least 4 hours prior to testing.

2. A 2041.2 grams (4.5 lb.) roller with a total diameter of 95 mm., the outer 6.7 mm. of which is rubber, is rolled over the sample from one end to the other and then back again (1 cycle).

3. The load cell is calibrated and the software loaded.

4. The grips are installed on the tensile tester with the jaws closed.

5. The test conditions for the tensile tester are set as follows:
Crosshead speed: 500 millimeters/minute
Full-scale load: 11.34 kilograms (25 lbs.)
Gage length: 25.4 millimeters (1 inch)

6. The weight of the clamp is tared out.

7. The sample is pulled apart on the end opposite from the enhanced refastenable attachment zone so that the fastening component and the mating fastening component disengage to form free ends each 25.4 millimeters long.

8. The free end of the fastening component on the back waist region of the article is inserted into the upper jaw.

9. The free end of the mating fastening component on the front waist region of the article is inserted into the lower jaw, such that the fastened inner surface of the back waist region and the fastened inner surface of the front waist region are facing the same direction and are parallel to one another. The lower jaw is closed.

10. The crosshead is started in motion, and the test is run until the fastening component and mating fastening component are no longer connected.

11. The average load needed to separate the fastener is recorded for the main refastenable attachment zone by averaging load values at separation distances that avoid any enhanced refastenable attachment zone, for example from 1 cm. by 6.4 cm. (0.4 to 2.5 inch) for the sample specified in the Sample Preparation section above. The peak load needed to separate the fastening components is recorded for the refastenable attachment zone(s). Two or more tests may be needed to obtain values for the refastenable attachment zones.

When introducing elements of the present disclosure or the preferred aspect(s) thereof, the articles "a", "an", "the", and "the" are intended to mean that there are one or more of the elements. The terms "comprising," "including", and "having" are intended to be inclusive and mean that there can be additional elements other than the listed elements.

The disclosure has been described with reference to various specific and illustrative aspects and techniques. However, it should be understood that many variations and modifications can be made while remaining within the spirit and scope of the disclosure. Many alternatives, modifications and variations will be apparent to those skilled in the art in light of the foregoing description. Accordingly, this disclosure is intended to embrace all such alternatives, modifications, and variations that fall within the spirit and scope of the appended claims.

I claim:

1. An absorbent article for personal wear about a wearer's waist, the article having a transverse axis and comprising:
   a liquid permeable inner surface for facing the wearer;
   an outer surface for facing away from the wearer;
   an absorbent body disposed therebetween;
   a front waist region and a back waist region each having side edges, and a crotch region extending longitudinally between and interconnecting the front and back waist regions;
   a pair of front side panels each having an attachment edge attached to a side edge of the front waist region and a pair of back side panels each having an attachment edge attached to a side edge of the back waist region, each side panel having a free edge opposite the attachment edge, each front side panel free edge being releasably attachable to the free edge of an associated back side panel using article fastening components to define a wear configuration of the absorbent article having a waist opening and a pair of leg openings spaced from the waist opening, wherein the front and back side panels each extend from the waist opening to one of the leg openings; and
   a finger tab extending from one of the back side panels, the finger tab having a distal end, a tab line where the finger tab intersects the free edge of the one of the back side panels, and a proximal end attached to the free edge of the one of the back side panels, wherein the distal end has a distal end longitudinal midpoint, wherein the tab line has a tab line longitudinal midpoint, and wherein the distal end longitudinal midpoint is longitudinally offset from the tab line longitudinal midpoint in a direction toward the waist opening, wherein the tab line has a tab line upper end, wherein the finger tab distal end has a lower edge, and wherein the distal end lower edge is further longitudinally offset from the article transverse axis than is the tab line upper end.

2. The article of claim 1, further comprising a waist edge, wherein the finger tab does not extend longitudinally beyond the waist edge.

3. The article of claim 1, the finger tab further comprising an engagement element.

4. The article of claim 1, wherein the finger tab has a recurve shape.

5. The article of claim 1, the finger tab further comprising a plurality of lanes of hook material.

6. The article of claim 1, wherein the finger tab is configured to be cut from a web of tab material without producing waste tab material.

7. The article of claim 1, wherein the longitudinal height of the distal end of the tab is equal to the longitudinal height of the tab line.

8. The article of claim 1, wherein the front and back side panels are attached in a lap seam.

9. The article of claim 1 wherein the finger tab is configured to engage the front side panel.

10. An absorbent article for personal wear about a wearer's waist, the article having an article transverse axis and comprising:
    a liquid permeable inner surface for facing the wearer;
    an outer surface for faring away from the wearer;
    an absorbent body disposed therebetween;
    a front waist region and a back waist region each having side edges, and a crotch region extending longitudinally between and interconnecting the front and back waist regions;
    a pair of front side panels each having an attachment edge attached to a side edge of the front waist region and a pair of back side panels each having an attachment edge attached to a side edge of the back waist region, each side panel having a free edge opposite the attachment edge, each front side panel free edge being releasably attachable to the free edge of an associated back side panel using article fastening components to define a wear configuration of the absorbent article having a waist opening and a pair of leg openings spaced from the waist opening, wherein the front and back side panels each extend from the waist opening to one of the leg openings; and
    a finger tab extending from one of the back side panels, the finger tab having a distal end, a tab line where the finger tab intersects the free edge of the one of the back: side panels, and a proximal end attached to the free edge of the one of the back side panels, wherein the distal end has a distal end longitudinal midpoint, wherein the tab line has a tab line longitudinal midpoint, wherein the finger tab has a tab central axis connecting the distal end longitudinal midpoint and the tab line longitudinal midpoint, wherein the tab central axis forms an acute angle with a line parallel to the transverse axis wherein the acute angle is greater than 45 degrees, and wherein the distal end longitudinal midpoint is longitudinally offset from the tab line longitudinal midpoint in a direction toward the waist opening.

11. The article of claim 10, wherein the acute angle is greater than 60 degrees.

* * * * *